(12) United States Patent
Morimura et al.

(10) Patent No.: US 12,310,905 B2
(45) Date of Patent: *May 27, 2025

(54) BED APPARATUS AND PATIENT DETECTION METHOD

(71) Applicant: PARAMOUNT BED CO., LTD., Tokyo (JP)

(72) Inventors: Hisao Morimura, Tokyo (JP); Makoto Tanaka, Tokyo (JP); Shinsuke Watanabe, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/547,976

(22) Filed: Dec. 10, 2021

(65) Prior Publication Data

US 2022/0096299 A1 Mar. 31, 2022

Related U.S. Application Data

(63) Continuation of application No. 14/361,761, filed as application No. PCT/JP2012/082153 on Dec. 12, 2012, now Pat. No. 11,246,778.

(30) Foreign Application Priority Data

Dec. 14, 2011 (JP) ................. 2011-273265

(51) Int. Cl.
*A61G 7/057* (2006.01)
*A61B 5/00* (2006.01)
(Continued)

(52) U.S. Cl.
CPC ........ *A61G 7/05776* (2013.01); *A61B 5/1113* (2013.01); *A61B 5/1117* (2013.01);
(Continued)

(58) Field of Classification Search
CPC .......... A61G 7/00; A61G 7/001; A61G 7/008; A61G 7/018; A61G 7/0525; A61G 7/057;
(Continued)

(56) References Cited

U.S. PATENT DOCUMENTS 5,003,654 A 4/1991 Vrzalik
5,092,007 A * 3/1992 Hasty ..................... A61G 7/001
5/691

(Continued)

FOREIGN PATENT DOCUMENTS

AU 2011 226 912-1 10/2011
CN 1146329 A 4/1997
(Continued)

OTHER PUBLICATIONS

Extended European Search Report dated Jul. 21, 2015 issued in corresponding EP Application No. 12858231.9.

*Primary Examiner* — Michelle J Lee
(74) *Attorney, Agent, or Firm* — BIRCH, STEWART, KOLASCH & BIRCH, LLP

(57) ABSTRACT

A bed apparatus includes: a mattress mounted on a bed body; and, first cells arranged on both left and right sides in a longitudinal direction of the bed body and is configured to change the body position of a patient on the mattress by inflating the first cells alternately. When the first cells on the left and right sides are inflated, and when a difference in pressure between the first cells on the left and right sides has continuously fallen within a decision pressure value range for a decision pressure value continuation time, the body position of the patient is changed, whereas when the difference has not continuously fallen within the pressure value range for the continuation time or when the difference has
(Continued)

continuously fallen out of the pressure value range for the continuation time, change of the body position of the patient will not be performed.

6 Claims, 7 Drawing Sheets

(51) Int. Cl.
 *A61B 5/11* (2006.01)
 *A61G 7/018* (2006.01)
(52) U.S. Cl.
 CPC ............ *A61B 5/6892* (2013.01); *A61G 7/018* (2013.01); *A61B 2503/08* (2013.01); *A61B 2505/03* (2013.01); *A61B 2505/07* (2013.01); *A61B 2562/0247* (2013.01); *A61G 2203/34* (2013.01); *A61G 2203/70* (2013.01)
(58) Field of Classification Search
 CPC ...... A61G 7/05738–05776; A61G 13/12–127; A47C 27/08–10; A61B 5/1113–1117; A61B 5/6892; A61B 2503/08; A61B 2505/03; A61B 2505/07; A61B 2562/0247; A61B 2203/34; A61B 2203/70
 See application file for complete search history.

(56) References Cited

U.S. PATENT DOCUMENTS

| | | | |
|---|---|---|---|
| 5,121,512 A | | 8/1992 | Kaufmann |
| 5,560,057 A | * | 10/1996 | Madsen ............. A61G 7/05776 5/713 |
| 5,592,706 A | | 1/1997 | Pearce |
| 5,745,942 A | | 5/1998 | Wilkerson |
| 5,802,640 A | | 9/1998 | Ferrand et al. |
| 5,926,883 A | | 7/1999 | Rechin et al. |
| 7,464,422 B2 | | 12/2008 | Townsend |
| 11,246,778 B2 | * | 2/2022 | Morimura ............. A61B 5/1113 |
| 2004/0177443 A1 | | 9/2004 | Simmonds et al. |
| 2007/0143928 A1 | | 6/2007 | Biggie et al. |
| 2011/0061164 A1 | | 3/2011 | Genaro |
| 2012/0317714 A1 | * | 12/2012 | Matschurek ........... A61G 7/001 5/81.1 RP |

FOREIGN PATENT DOCUMENTS

| | | | |
|---|---|---|---|
| DE | 102005046486 A1 * | 4/2006 | ............ A61B 5/103 |
| EP | 1 292 259 A2 | 3/2003 | |
| JP | 9-253137 A | 9/1997 | |
| JP | 11-76318 A | 3/1999 | |
| JP | 2004-194709 A | 7/2004 | |
| JP | 2010-155084 A | 7/2010 | |
| JP | 2010-253192 A | 11/2010 | |

* cited by examiner

BED APPARATUS AND PATIENT DETECTION METHOD

CROSS-REFERENCE TO RELATED APPLICATIONS

This application is a Continuation of copending application Ser. No. 14/361,761, filed on May 30, 2014, which was filed as PCT International Application No. PCT/JP2012/082153 on Dec. 12, 2012, which claims the benefit under 35 U.S.C. § 119(a) to Patent Application No. 2011-273265, filed in Japan on Dec. 14, 2011, all of which are hereby expressly incorporated by reference into the present application.

TECHNICAL FIELD

The present invention relates to a bed apparatus and the like that includes a mattress mounted on a bed body and first cells arranged on both the left and right sides in the longitudinal direction of the bed body and changes the body position of the patient on the mattress by inflating the first cells alternately.

BACKGROUND ART

Conventionally, in order to prevent bed ridden patients and severely injured patients from suffering bedsores, there have been known mattresses (bed apparatus) that change the body position of the patient (e.g., see Patent Document 1). For example, there are mattresses (bed apparatus) that have a function of turning the patient lying in the supine position to the 30 degree side elevated supine position and/or a function of performing 40 degree continuous left and right side rotation as a respiratory physiotherapy.

PRIOR ART DOCUMENT

Patent Document

Patent Document 1:
  Japanese Patent Application Laid-open H09-253137

SUMMARY OF THE INVENTION

Problems to be Solved by the Invention

Herein, when the body position of a patient is changed, the position where the patient stays on the mattress should be considered. That is, if the function of changing the body position is used when the patient is lying in a displaced position or when the patient stays along the bed edge, there is a risk of the patient passing over the bed rails and falling. In order to prevent the patient from falling, the user has to monitor the patient at any time, which is a big burden.

In view of the above problem, it is therefore an object of the present invention to provide a bed apparatus and the like that can detect the place of the patient lying on the bed before changing the body position of the patient to prevent the patient from falling from the bed apparatus.

Means for Solving the Problems

In order to solve the above problem, a bed apparatus of the present invention comprises:
  a mattress mounted on a bed body; and,
  first cells arranged on both left and right sides in a longitudinal direction of the bed body,
wherein the bed apparatus is configured to change the body position of a patient on the mattress by inflating the first cells alternately,
  the first cells on the left and right sides are inflated, and
  when a difference in pressure between the first cells on the left and right sides has continuously fallen within a decision pressure value range fora decision pressure value continuation time, the body position of the patient is changed, and
  when the difference in the pressure between the first cells on the left and right sides has not continuously fallen within the decision pressure value range for the decision pressure value continuation time or when the difference in the pressure between the first cells on the left and right sides has continuously fallen out of the decision pressure value range for the decision pressure value continuation time, change of the body position of the patient will not be performed.

The bed apparatus of the present invention further comprises second cells arranged on both the left and right sides in the longitudinal direction of the mattress to support the patient, wherein, instead of the first cells, the second cells on the left and right sides are inflated, and
  when a difference in pressure between the second cells on the left and right sides has continuously fallen within a decision pressure value range fora decision pressure value continuation time, the position of the patient is changed, and
  when the difference in the pressure between the second cells on the left and right sides has not continuously fallen within the decision pressure value range for the decision pressure value continuation time or when the difference in the pressure between the second cells on the left and right sides has continuously fallen out of the decision pressure value range for the decision pressure value continuation time, change of the body position of the patient will not be performed.

A patient detecting method of the present invention is used for a bed apparatus comprising: a mattress mounted on a bed body; and, first cells arranged on both left and right sides in a longitudinal direction of the bed body, the bed apparatus being configured to change a body position of a patient on the mattress by inflating the first cells alternately when the patient stays around a center of the mattress, and the method comprises the steps of:
  inflating the first cells on the left and right sides;
  detecting the patient staying in the center of the mattress from the fact that a difference in pressure between the first cells on the left and right sides has continuously fallen within a decision pressure value range for a decision pressure value continuation time, and
  detecting the patient staying near an edge of the mattress when the difference in the pressure between the first cells on the left and right sides has not continuously fallen within the decision pressure value range for the decision pressure value continuation time or when the difference in the pressure between the first cells on the left and right sides has continuously fallen out of the decision pressure value range for the decision pressure value continuation time.

Advantages of the Invention

According to the present invention, the bed apparatus of the present invention is comprising: the mattress mounted on the bed body; and, first cells arranged on both the left and right sides in the longitudinal direction of the bed body, to change the body position of the patient on the mattress by inflating the first cells alternately. The first cells on the left and right sides are inflated, and when the difference in the pressure between the first cells on the left and right sides has continuously fallen within the decision pressure value range for the decision pressure value continuation time, the body position of the patient is changed, whereas when the difference in the pressure between the first cells on the left and right sides has not continuously fallen within the decision pressure value range for the decision pressure value continuation time or when the difference in the pressure between the first cells on the left and right sides has continuously fallen out of the decision pressure value range for the decision pressure value continuation time, change of the body position of the patient will not be performed. That is, when the pressure difference has not continuously fallen within the decision pressure value range for the decision pressure value continuation time, it is detected that the patient is not staying in the center of the mattress, the rotating function is stopped so that the patient will not fall as a result of the rotating function.

MODE FOR CARRYING OUT THE INVENTION

Next, the best mode for carrying out the present invention will be described with reference to the drawings. Here, the following embodied mode is an example for explaining the invention, the numerical values and others should not be of course limited to those described in the present embodiment.

1. SCHEMATIC DESCRIPTION OF THE APPARATUS

[1.1 Overall Description]

Figure 1:
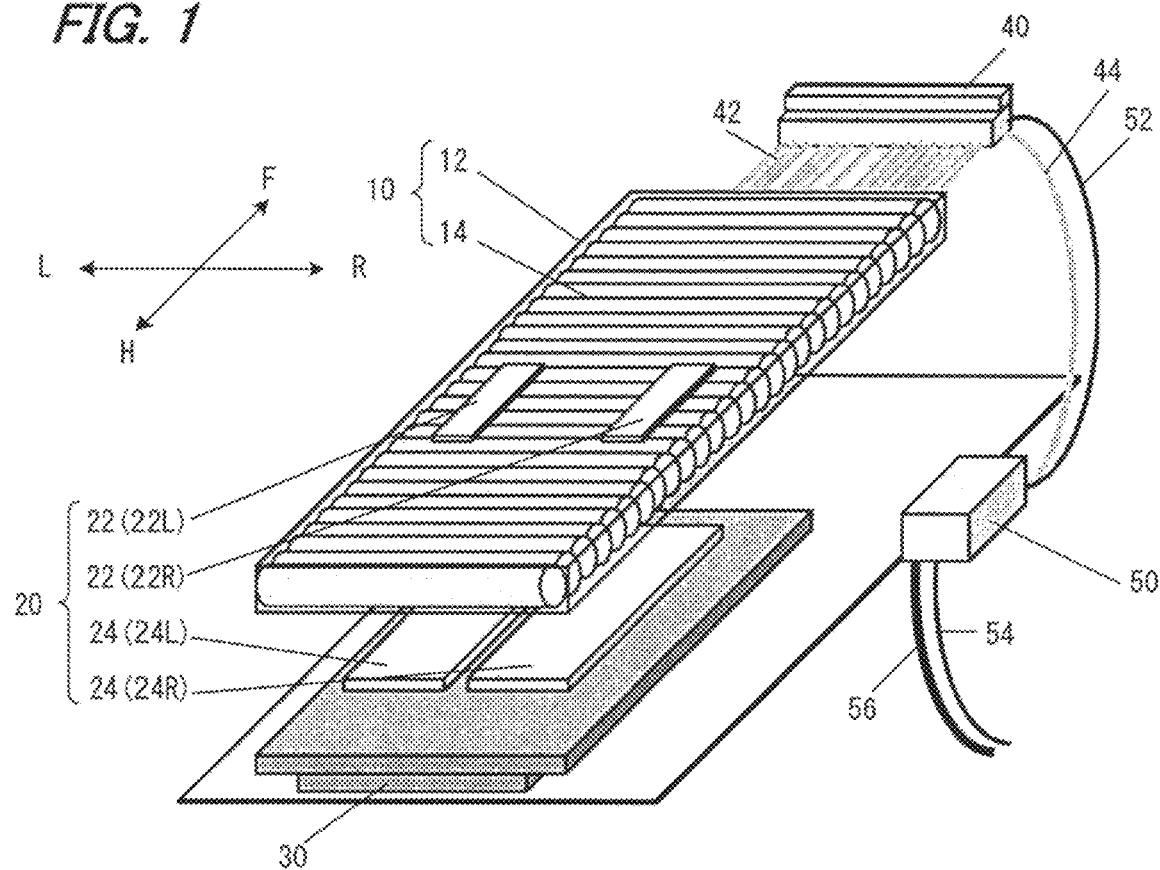
FIG. 1 A diagram for illustrating the overall structure of a bed apparatus in the present embodiment.
Figure 2:
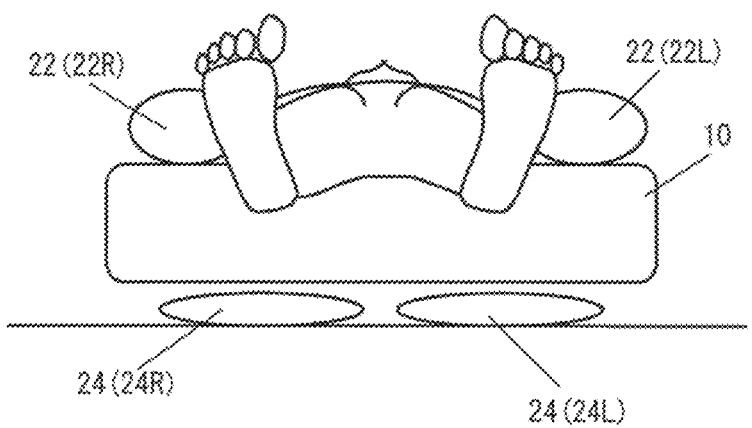
FIG. 2 A diagram for illustrating the overall structure of the bed apparatus in the present embodiment.

To begin with, the overall configuration of the bed apparatus to which the present invention is applied will be described with reference to FIGS. 1 and 2. FIG. 1 is the diagram for illustrating the overview of the bed apparatus 1 in the present embodiment. FIG. 2 is a front view showing bed apparatus 1, viewed from the foot side (the controller 40 side in FIG. 1).

Bed apparatus 1 includes a mat body 10 mounted on a base 30. Herein, mat body 10 is formed of a plurality of cells 14 arranged contiguously in the longitudinal direction. These cells are enfolded by a cover 12 of a top cover and a bottom cover, to form mat body 10.

Bed apparatus 1 also includes a rolling portion 20. Rolling structure 20 is formed of side cells 22 and rolling cells 24 to be used for changing the body position of the patient.

Herein, bed apparatus 1 is used with the patient foot side oriented in the direction of F (to the controller 40 side) in FIG. 1 and the head side in the direction of H in FIG. 1. Accordingly, the R-direction is on the right side of the patient in FIG. 1 and the L-direction is on the left side in FIG. 1.

Side cells 22 are formed of a side cell 22R on the right side and a side cell 22L on the left side. Rolling cells 24 are formed of a rolling cell 24R on the right side and a rolling cell 24L on the left side.

Connected to individual cells (cells 14, side cells 22, rolling cells 24) are air blow tubes 42 from controller 40. An air blow tube 44 from a pump unit 50 is connected to controller 40. Further, controller 40 and pump unit 50 are connected to each other by a control cable 52 so that various control signals are exchanged therebetween. Connected to pump unit 50 are a control cable 54 from without and a power cable 56 for driving the pump.

Individual cells 14 are separated into plural branch groups, the cells of each branch group being connected to a common air blow tube 42 as a communication path. Air blow tube 42 is connected to selector valves by way of an air blow tube connector. The selector valves are connected to pump unit 50 by way of air blow tube 44. Thus, the operation of pump unit 50 and the selector valves inflates and deflates individual cells.

Similarly to the inflating and deflating operation of these cells 14, side cells 22 and rolling cells 24 are also connected to air blow tubes 42 and connected to selector valves via air blow tubes 42. The selector valves are connected to pump 50 via air blow tubes 44 so as to perform inflation and deflation.

Here, air blow tubes 42 as the communication paths may be constructed so that a single tube output from pump unit 50 is branched into plural tubes, or so that a plurality of tubes are output from pump unit 50. In other words, any configuration may be accepted as long as each cell can be made to take the same pressure value with others in making each cell communicate with others.

[1.2 Explanation of the Individual Cell Configuration]

Figure 3:
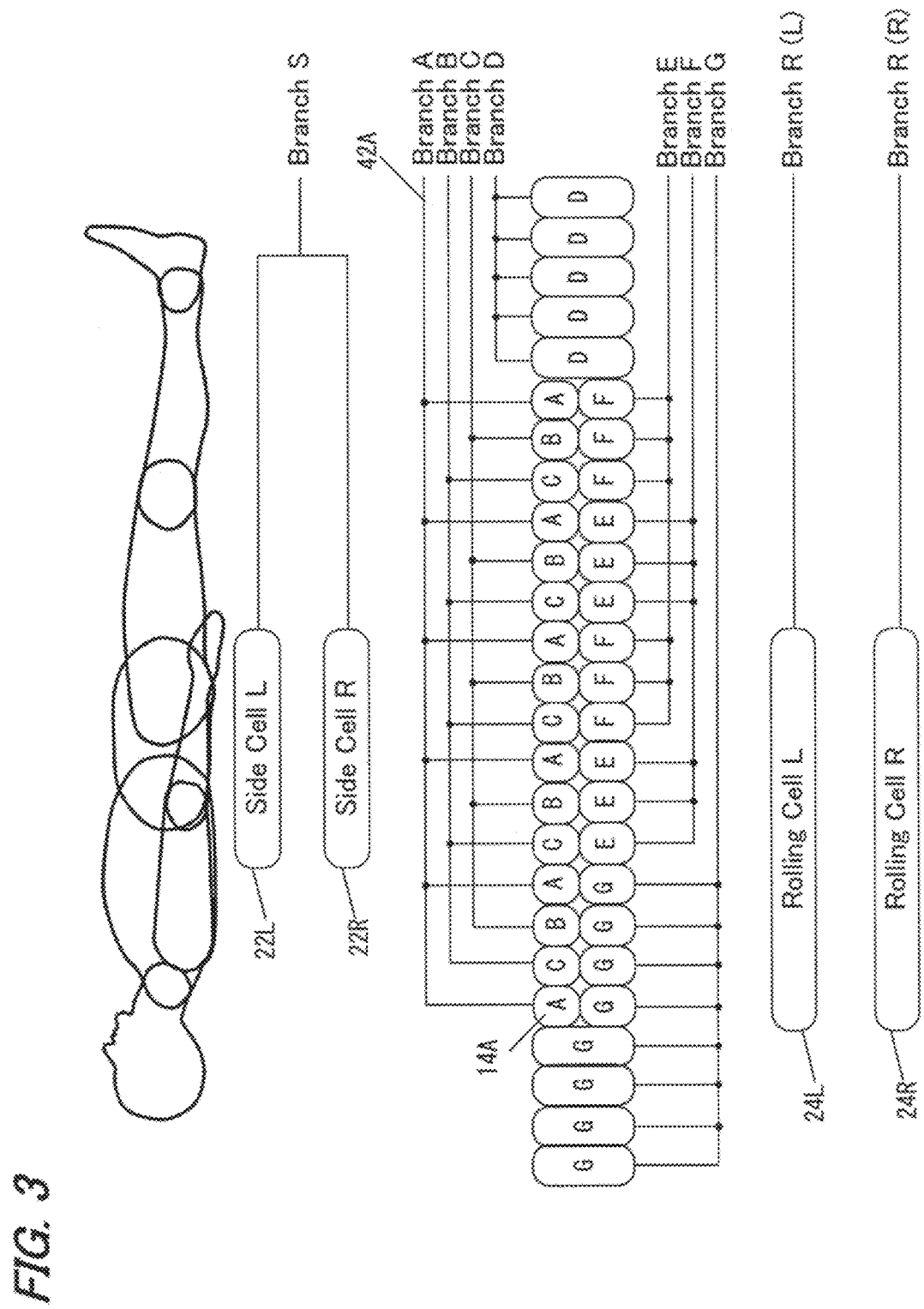
FIG. 3 A diagram for illustrating individual cells of the bed apparatus in the present embodiment.

Next, the configuration of each cell (cell 14, side cell 22 and rolling cell 24) will be described with reference to FIG. 3. As shown in FIG. 3, side cells 22 are connected as a branch S to pump 50 via the selector valve while rolling cells 24 connected as branches (rolling cell L as branch R(L) and rolling cell R as branch R(R)) to the pump 50 via sector valves.

The cells are separated into branches A to G, each connected to pump unit 50. For example, cells 14A are connected to air blow tube 42A as branch A. All cells 14A belonging to branch A are equally inflated or deflated by air blow tube 42A.

2. FUNCTIONAL CONFIGURATION

Figure 4:
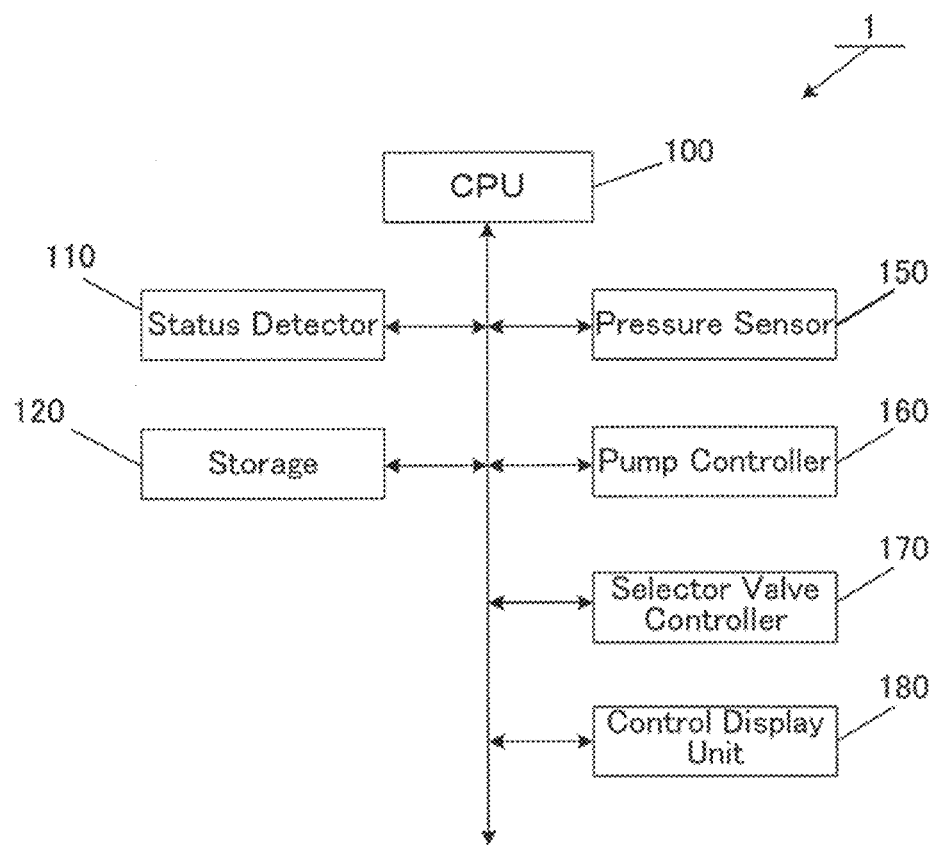
FIG. 4 A diagram for illustrating the configuration of functions in the present embodiment.

Next, the functional configuration of bed apparatus 1 will be described using FIG. 4. In bed apparatus 1, CPU 100 is connected to a status detector 110, a storage 120, a pressure sensor 150 and a pump controller 160, as shown in FIG. 4.

CPU (Central Process Unit) 100 is a functional unit for controlling bed apparatus 1 as a whole. CPU 100 implements diverse functions by reading and executing various programs stored in storage 120.

Status detector 110 is a functional unit for detecting various states in bed apparatus 1. For example, the detector detects the state by detecting the states of the pressure sensor and detecting the operational signals of the actuators. Herein, as the states to be detected, various states can be detected such as, for example, the back rise angle of the bed, the leg lowering angle, the weight of the patient, and the stay-in-bed state of the patient.

Storage 120 is a functional unit that stores various programs, and various data, required to operate bed apparatus 1. Storage 120 is configured of, for example semiconductor memories, HDD (Hard Disk Drive) and the like.

Pressure sensor 150 is a functional unit for detecting the pressure of each cell, and is configured of a pressure sensor and the like. Pressure sensor 150 is connected to each selector valve (for each cell branch) via an air blow tube joint connector. The pressure of each cell is detected by pressure sensor 150.

Pump controller 160 is a functional unit for controlling pump unit 50. Control on inflation and deflation can be implemented by activating and deactivating pump unit 50.

A selector valve controller 170 is a functional unit for controlling the selector valve connected to each branch of cells and the selector valve connected to pump unit 50. By controlling the selector valves, it is possible to perform control of inflating the cells and deflating the cells in cooperation with the operation of pump unit 50. It is possible to perform control of retaining the air in each cell.

A control display unit 180 severs as an input unit for users (e.g., patients, care-receivers, caregivers, etc.) to instruct the operation to drive bed apparatus 1 and as a functional unit for notifying the user of the conditions of bed apparatus 1. This unit can be configured of a liquid crystal screen including a touch panel or hardware keys, for example.

3. PROCESSING FLOW

Figure 5:
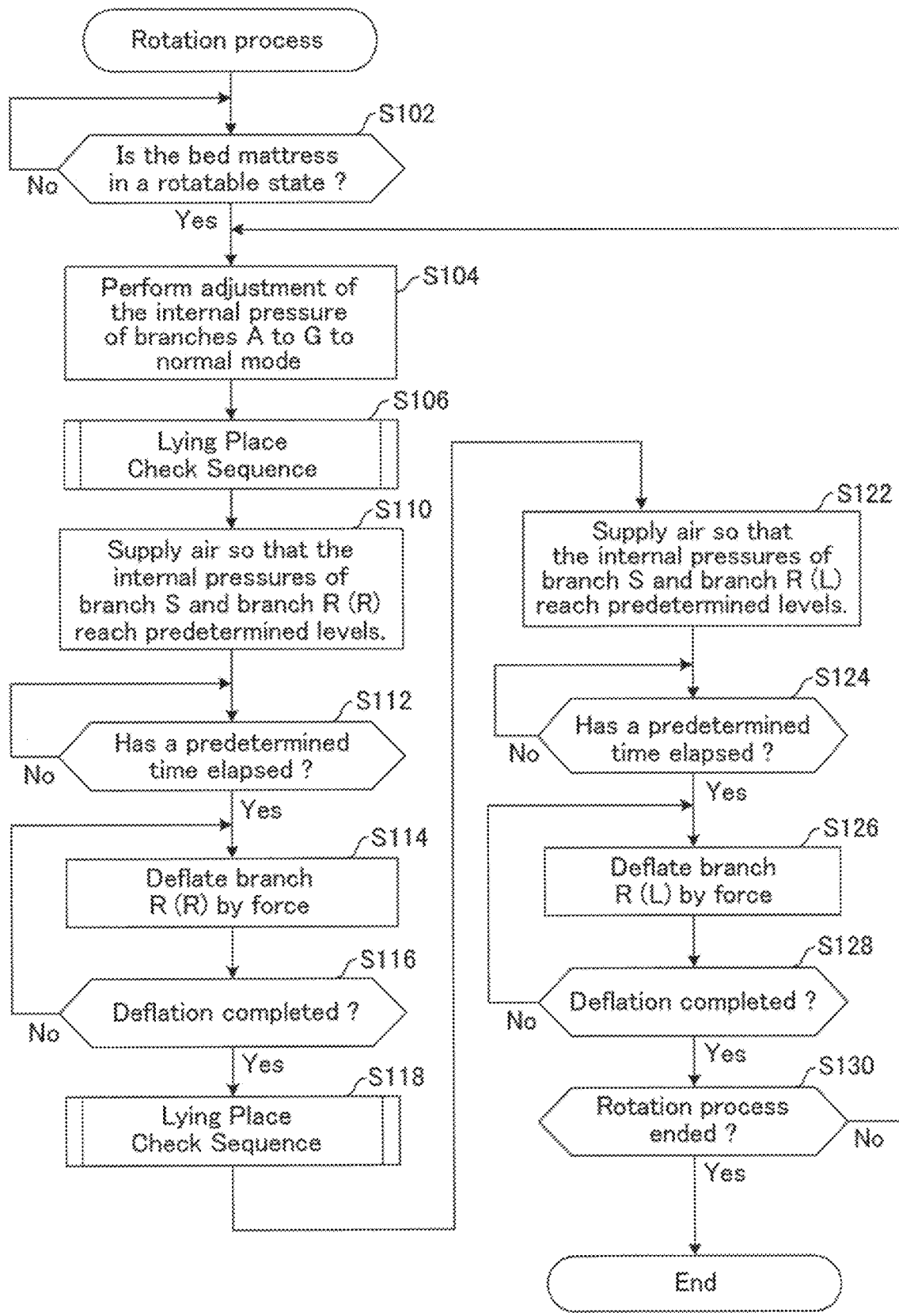
FIG. 5 An operation flow for illustrating a rotation process in the present embodiment.

Next, the processing flow will be described using the drawings. FIG. 5 shows a flow regarding a rotation process in the present embodiment.

To begin with, it is determined whether or not the mattress is in a rotatable state (Step S102). Here, the rotatable state is determined by checking whether or not the current state, for example satisfies the following operating conditions:
the back angle of the bed is less than 4 degrees;
the knee angle is less than 4 degrees;
the leg angle is less than 4 degrees;
the tilt angle of the bed apparatus is 4 degrees or smaller; and,
the operation mode is in the normal mode.

Then, when the above operational conditions are satisfied (Step S102; Yes), the cells of branches A to G are adjusted to the internal pressure in the normal mode (Step S104). Subsequently, a lying place check sequence for checking the place of the lying patient is implemented (Step S106).

Now, the lying place check sequence will be described using FIG. 6. First, branch R(R) is inflated by the decision-preparatory time (Step S202). As to branch R(L), air is supplied by the decision-preparatory time (Step S204).

Herein, the decision-preparatory time is a period (10 seconds, for example) provided for supplying a predetermined amount of air to the left and right cells of branch R in order to confirm that the patient is staying around the center of the bed device. Though in the present embodiment, inflation is performed based on time, inflation may be determined based on the amount of air, for example. Further, for description convenience, inflation is performed at Step S202 and Step S204, but branch R(R) and branch R(L) may be inflated alternately, simultaneously, or separately.

After the end of inflating branch R(R) and branch R(L), difference in pressure value (LR differential pressure value) between branch R (R) and branch R (L) is calculated (Step S206). Then, after passage of a decision pressure value continuation time (Step S208; Yes), it is determined whether or not the LR differential pressure value has been continuously detected to fall out of a decision pressure value range for the decision pressure value continuation time (Step S210). At this stage, if the LR differential pressure value has been continuously detected to fall out of the decision pressure value range for the decision pressure value continuation time (Step S210; Yes), it is determined that an error took place, and the rotation process is stopped.

On the other hand, when the LR differential pressure value has not been continuously detected to fall out of the decision pressure value range for the decision pressure value continuation time but the detected LR differential pressure value has not become lower than a predetermined decision pressure value for the decision pressure value continuation time, the rotation process is stopped (Step S210; No→Step S212; No).

As an example, it is determined whether or not the LR differential pressure value hovers less than the decision pressure value (e.g., "1 kPa") and the total time in which this condition has been satisfied is "7 seconds" or more among "10 seconds" for example. Alternatively, it is determined whether or not the LR differential pressure value has been continuously less than the decision pressure value for "5 seconds".

That is, when, in accordance with the predetermined condition, the LR differential pressure value has not been detected within the decision pressure value range for the decision pressure continuation time, or the LR differential pressure value has been continuously detected out of the decision pressure value range for the decision pressure continuation time (Step S210; Yes/Step S210; No→Step S212; No), the lying place check sequence stops the rotation process.

On the other hand, when, in accordance with the predetermined condition, the LR differential pressure value has been detected within the decision pressure value range for the decision pressure continuation time (Step S212; Yes), branch R (R) is deflated by force (Step S214) and branch R(L) is deflated by force (Step S216). Here, deflation of branch R(R) and branch R(L) may be performed alternately or simultaneously. Further, forced deflation may be implemented until the internal pressure reaches a predetermined level or atmospheric pressure.

Returning to Step S106 of FIG. 5, the process will be described. After the lying place check sequence has been implemented, branch S and branch R(R) are inflated until the internal pressure reach predetermined levels (Step S110).

After passage of a predetermined period (Step S112; Yes), branch R(R) is deflated by force (Step S114). Then, as deflation is complete (Step S116; Yes), the lying place check sequence is implemented (Step S118). That is, the lying place of the patient is checked before implementation of the rotating function in branch R(L).

After implementation of the lying place check sequence, air is supplied so that the internal pressures of branch S and branch R(L) reach a predetermined level (Step S122). After passage of a predetermined period (Step S124; Yes), branch R(L) is deflated by force (Step S126).

After the end of deflation (Step S128; Yes), it is determined whether or not the rotation process should be ended (Step S130). At this step, when the rotation process is ended, the process is ended (Step S130; Yes). When the process is continued, the same control from Step S104 is repeated (Step S130; No).

In the above way, according to the present embodiment, when the rotation process is implemented, the lying place of the patient is always checked. Accordingly, it is possible to avoid improper rotation due to the fact that the patient stays close to the edge instead of residing in the center of the bed apparatus. Further, it is possible to avoid the patient falling as a result of implementation of the rotating function when the patient is staying near the edge.

4. VARIATIONAL EXAMPLES

As the embodiment of this invention has been detailed with reference to the drawings, the specific configuration should not be limited to this embodiment. Designs and others that do not depart from the gist of this invention should also be included in the scope of claims.

The predetermined pressure values, ranges and time referred to in the above embodiment are given with specific values in order to enhance understanding of the present invention. Accordingly, the present invention should not be limited by these values.

Further, though in the above embodiment check of the lying place in the lying place check sequence is performed using the cells of branch R, check of the lying place may be performed using the cells of branch S. A case using the cells of branch S will be described using FIG. 7.

Figure 6:
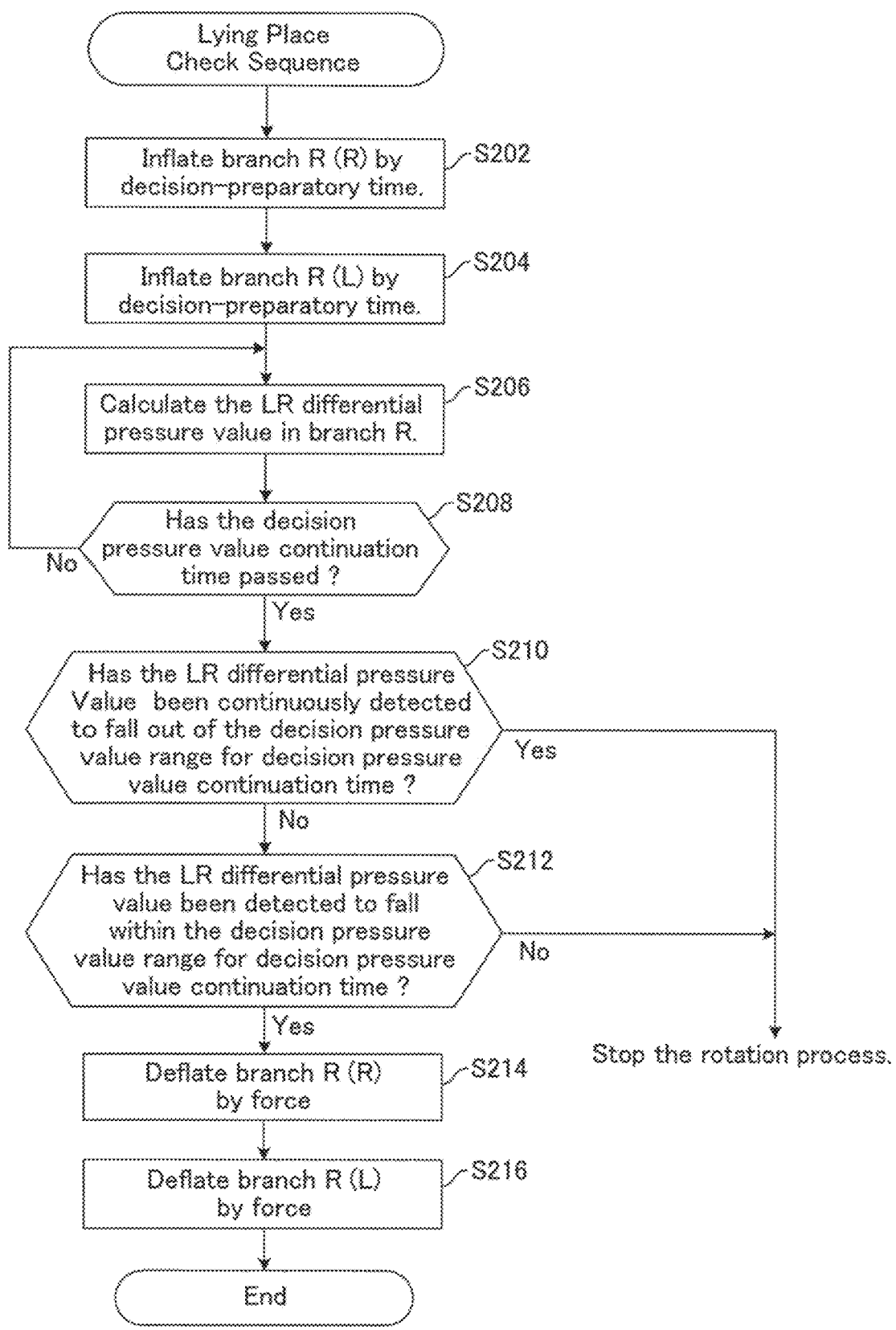
FIG. 6 An operation flow for illustrating a sequence of checking the lying place in the present embodiment.
Figure 7:
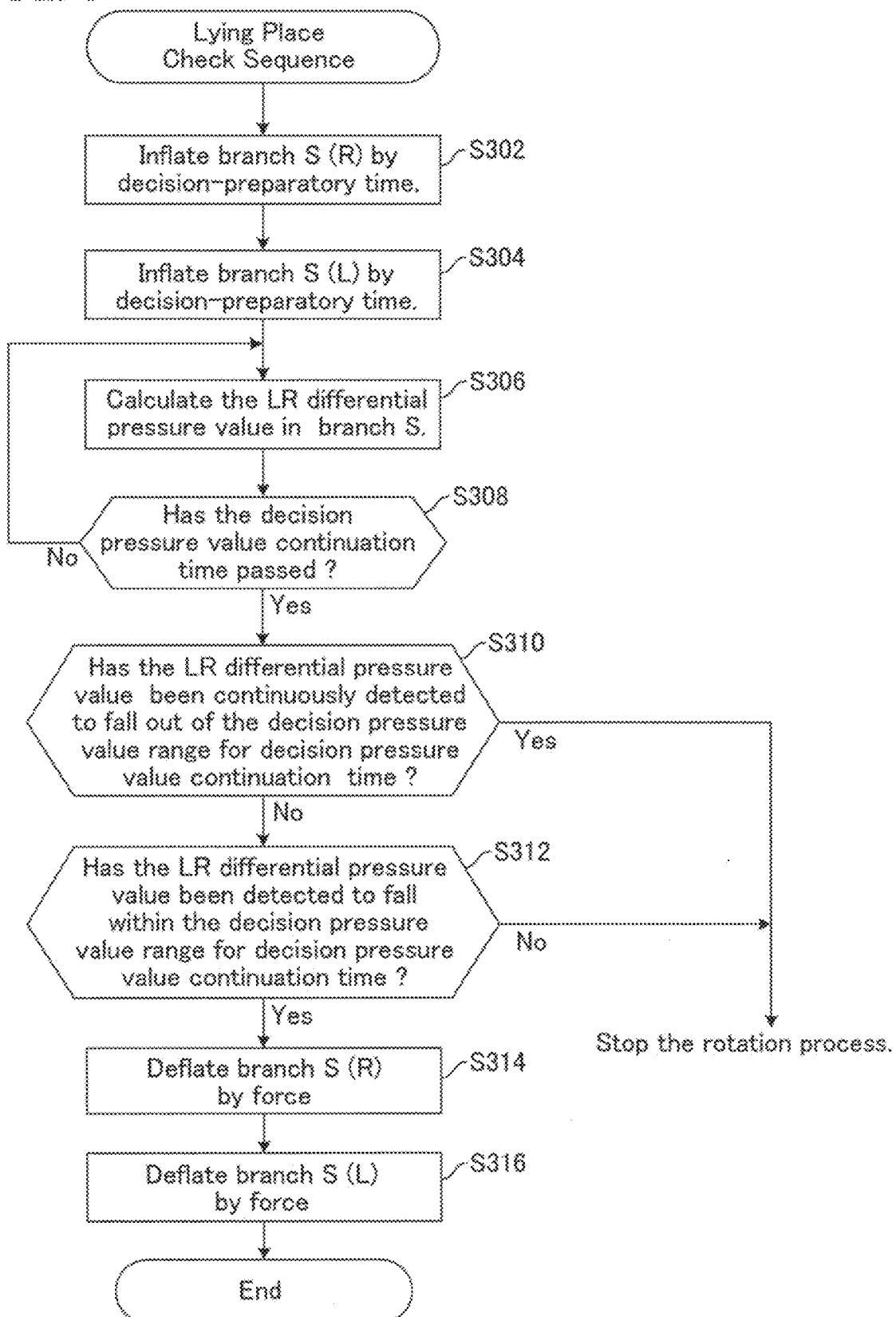
FIG. 7 A diagram for illustrating a variational example of the present embodiment.

FIG. 7 shows the lying place check sequence described in FIG. 6 in which branch R is replaced by branch S. FIG. 7 shows the same sequence other than this. Briefly describing with FIG. 7, first, branch S(R) and branch S(L) are inflated by the decision-preparatory time (Steps S302 and S304). Then, the LS differential pressure in branch S is calculated (Step S306).

After passage of the decision pressure value continuation period (Step S308; Yes), if it is determined that in accordance with the predetermined condition the LR differential pressure value has not been detected within the decision pressure value range for the decision pressure value continuation time or the LR differential pressure value has been continuously detected to fall out of the decision pressure value range for the decision pressure value continuation time (Step S310; Yes/Step S310; No→Step 312: No), the rotation process is stopped. On the other hand, when, in accordance with the predetermined condition, the LR differential pressure value has been detected within the decision pressure value range for the decision pressure continuation time (Step S310; No→Step S312; Yes), branch S(R) and branch S(L) are deflated by force (Step S314 and Step S316).

In this way, it is possible to implement the lying place check sequence using branch S instead of using branch R.

Further, the above-described embodiment has been described by giving an example in which a cell is divided into multiple sections (an example where the cells located near the center are divided into upper and lower sections). However, each cell may be simply formed of a single part.

Figure 8:
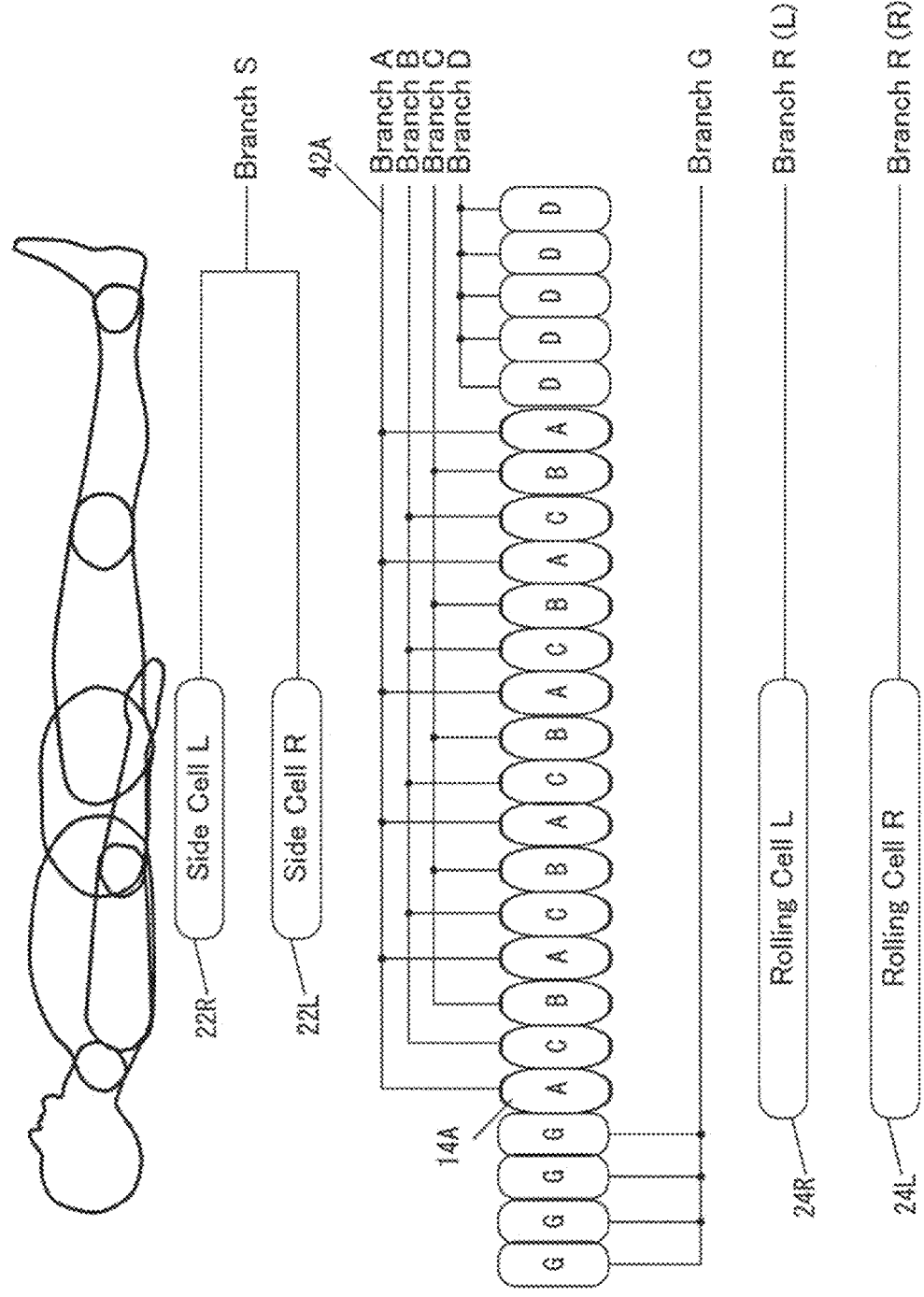
FIG. 8 A diagram for illustrating a variational example of the present embodiment.

For example, as shown in FIG. 8, the cells may be simply arranged in the longitudinal direction without being divided into upper and lower sections, to form the entire air mattress.

Further, though the above embodiments were described by using an air mattress as the mattress, it is possible to implement a rotating function by using mattresses of other materials such as urethane mattresses, and water mattress. It is apparent that the present invention can also be applied to those cases.

DESCRIPTION OF REFERENCE NUMERALS 1 bed apparatus
10 mat body
12 cover
14 cell
14a, 14b, 14c cell branch
10 rolling portion
22, 22L, 22R side cell
24, 24L, 24R rolling cell
30 base
40 controller
42, 44 air blow tube
50 pump unit
53 control cable
54 control cable
56 power cable
100 CPU
110 status detector
120 storage
150 pressure sensor
160 pump controller
170 selector valve controller
180 control display unit

The invention claimed is:

1. A bed apparatus comprising:
a mattress mounted on a bed body; and
a first cell arranged on a left side of the bed body;
a second cell arranged on a right side of the bed body;
a display;
a controller configured to:
during a rotation operation, perform a first operation to determine a body position of auser of the bed apparatus,
cause the display to notify the user of conditions of the bed apparatus,
confirm whether the user is staying at a center of the bed apparatus by performing the first operation, which includes inflating the first and second cells and calculating a difference in pressure between the first and second cells;
wherein if the difference in pressure has continuously fallen within a predetermined range for a first period, perform the rotation operation to inflate the first cell and the second cell alternately after exhausting air to deflate both the first cell and the second cell once, wherein the controller is configured not to perform the rotation operation if the difference in pressure has not continuously fallen within the predetermined range for the first period.

2. The bed apparatus according to claim 1, wherein the first cell and the second cell extends in a longitudinal direction of the bed body.

3. The bed apparatus according to claim 2, wherein the controller is configured to perform the rotation operation after exhausting air to deflate both the first cell and the second cell once, if the difference in pressure between the first cell and the second cell has continuously fallen within the predetermined range after the controller inflates both the first cell and the second cell during a second period.

4. The bed apparatus according to claim 1, wherein the controller is configured to perform the rotation operation after exhausting air to deflate both the first cell and the second cell once, if the difference in pressure between the first cell and the second cell has continuously fallen within the predetermined range after the controller inflates both the first cell and the second cell during a second period.

5. The bed apparatus according to claim 1, further comprising:
   third cells arranged on the bed body, the third cells extending in a first direction which is different from a second direction, the first and second cells extending in the second direction.

6. The bed apparatus according to claim 1, wherein, during the first operation,
   the controller is configured to determine whether or not the difference in pressure has been continuously detected to fall out of the predetermined range for the first period,
   or whether the difference in pressure has been detected within the predetermined range for the first period.

* * * * *